(12) United States Patent
Gao

(10) Patent No.: US 7,780,915 B2
(45) Date of Patent: Aug. 24, 2010

(54) FECAL SAMPLE TEST DEVICE AND METHODS OF USE

(75) Inventor: Ping Gao, San Diego, CA (US)

(73) Assignee: Epitope Diagnostcs, Inc., San Diego, CA (US)

( * ) Notice: Subject to any disclaimer, the term of this patent is extended or adjusted under 35 U.S.C. 154(b) by 0 days.

(21) Appl. No.: 11/354,501

(22) Filed: Feb. 15, 2006

(65) Prior Publication Data
US 2006/0188939 A1 Aug. 24, 2006

Related U.S. Application Data

(60) Provisional application No. 60/653,345, filed on Feb. 16, 2005.

(51) Int. Cl.
*B01L 3/00* (2006.01)
*G01N 33/566* (2006.01)

(52) U.S. Cl. .................... 422/58; 422/61; 422/68.1; 435/4; 435/7.1; 435/286.4; 435/286.7; 435/287.1; 435/287.6; 501/1

(58) Field of Classification Search .............. 422/58, 422/61, 68.1; 435/4, 7.1, 286.4, 286.7, 287.1, 435/287.2, 287.6; 436/501, 518, 165; 501/501, 501/518, 165
See application file for complete search history.

(56) References Cited

U.S. PATENT DOCUMENTS

| | | | |
|---|---|---|---|
| 4,539,180 A * | 9/1985 | Schwartz | ..................... 422/58 |
| 4,770,853 A | 9/1988 | Bernstein | |
| 4,943,522 A | 7/1990 | Eisinger | |
| 4,978,504 A | 12/1990 | Nason | |
| 5,250,412 A | 10/1993 | Giegel | |
| 5,275,785 A | 1/1994 | May | |
| 5,415,994 A | 5/1995 | Imrich | |
| 5,602,040 A | 2/1997 | May | |
| 5,622,871 A | 4/1997 | May | |
| 5,654,162 A | 8/1997 | Guire | |
| 5,656,503 A | 8/1997 | May | |
| 5,658,531 A | 8/1997 | Cope | |
| 5,714,389 A | 2/1998 | Charlton | |
| 5,869,003 A | 2/1999 | Nason | |
| 5,877,028 A | 3/1999 | Chandler | |
| 5,879,635 A | 3/1999 | Nason | |
| 5,965,453 A | 10/1999 | Skiffington | |
| 5,965,456 A | 10/1999 | Malmqvist | |
| 6,020,147 A | 2/2000 | Guire | |
| 6,074,606 A | 6/2000 | Sayles | |
| 6,156,271 A | 12/2000 | May | |
| 6,187,598 B1 | 2/2001 | May | |
| 6,228,660 B1 | 5/2001 | May | |
| 6,271,046 B1 | 8/2001 | Chandler | |
| 6,352,862 B1 | 3/2002 | Davis | |
| 6,372,516 B1 | 4/2002 | Sun | |
| 6,375,896 B1 | 4/2002 | Wuske | |
| 6,485,982 B1 | 11/2002 | Charlton | |
| 6,534,320 B2 | 3/2003 | Ching | |
| 6,663,833 B1 | 12/2003 | Stave et al. | |
| RE38,430 E | 2/2004 | Rosenstein | |
| 6,818,455 B2 | 11/2004 | May | |
| 6,890,484 B2 | 5/2005 | Bautista | |
| 6,924,153 B1 * | 8/2005 | Boehringer et al. | ......... 436/514 |
| 7,090,803 B1 * | 8/2006 | Gould et al. | ................. 422/58 |
| 7,098,040 B2 * | 8/2006 | Kaylor et al. | ............... 436/514 |
| 7,241,417 B2 * | 7/2007 | Lee et al. | ...................... 422/58 |
| 2002/0173047 A1 * | 11/2002 | Hudak et al. | ................ 436/178 |
| 2003/0021727 A1 * | 1/2003 | Weyker et al. | ............... 422/58 |
| 2005/0106750 A1 * | 5/2005 | Tung et al. | .................. 436/169 |
| 2005/0112023 A1 * | 5/2005 | Liang | .......................... 422/58 |

* cited by examiner

*Primary Examiner*—Lisa V Cook
(74) *Attorney, Agent, or Firm*—Biotech Beach Law Group PC; Raymond Wagenknecht

(57) ABSTRACT

The present invention includes devices and methods for the detection of an analyte in a fecal sample. The fecal sample test device includes a sample collection structure and sample collection housing, a detection housing, a fecal suspension solution or fecal dilution solution, a detection housing capable of attachment to the collection housing and an analyte detecting means. When attached, the collection housing permits a portion of liquid extracted sample to fluidly flow into the detection housing where the analyte detection means detects the presence or quantity of an analyte suspected of being present in the fecal sample.

24 Claims, 6 Drawing Sheets

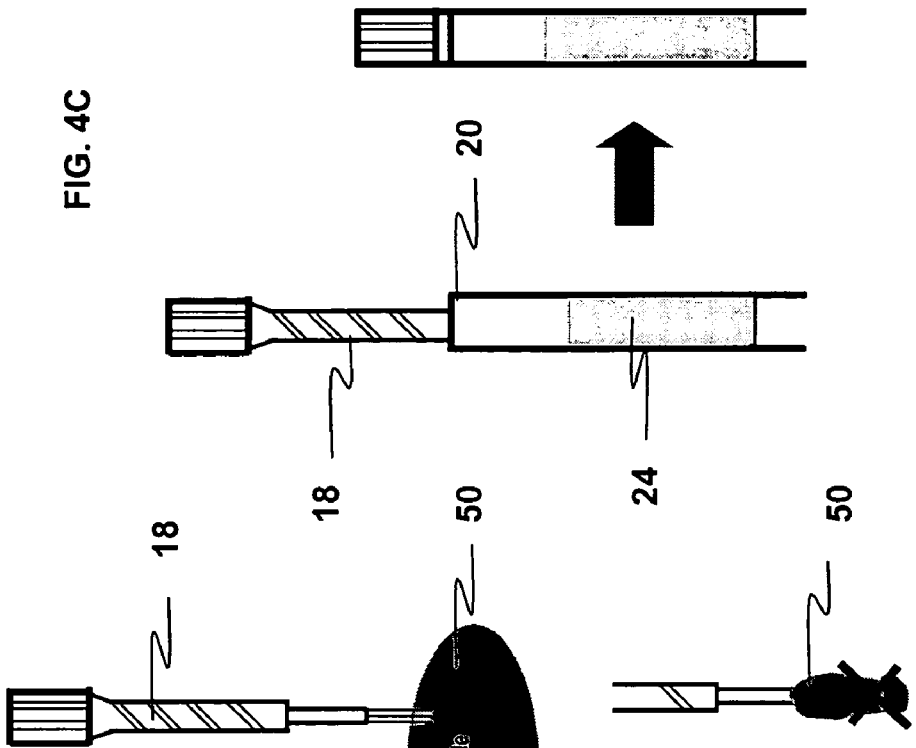
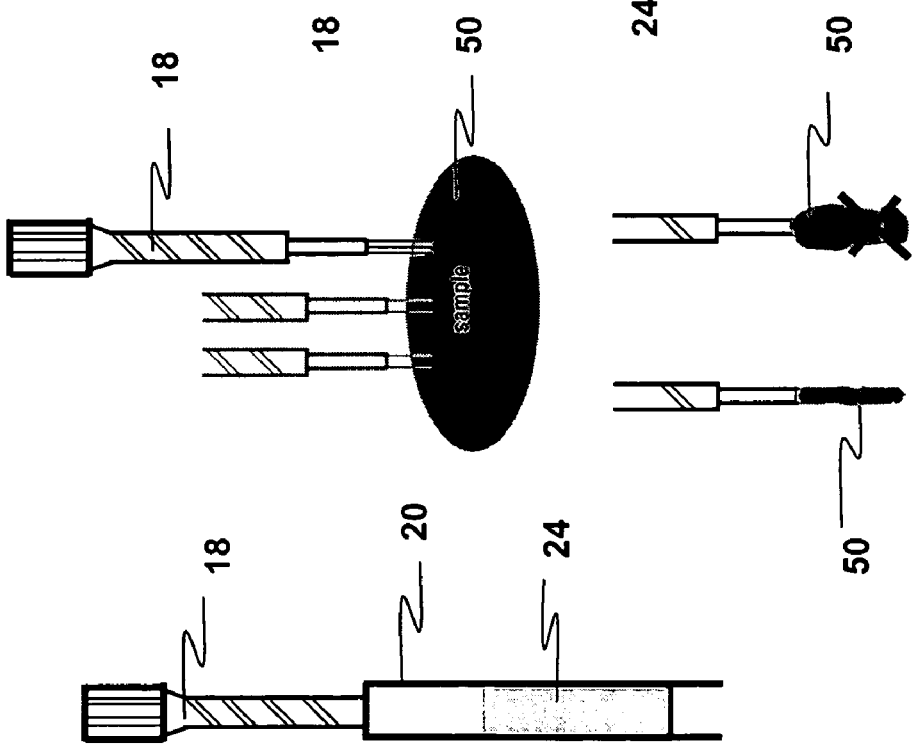
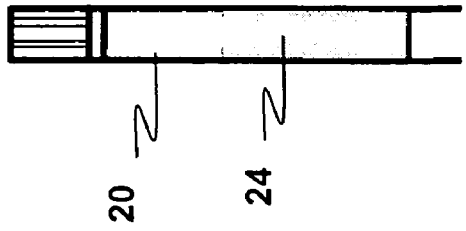
FIG. 4C
FIG. 4B
FIG. 4A

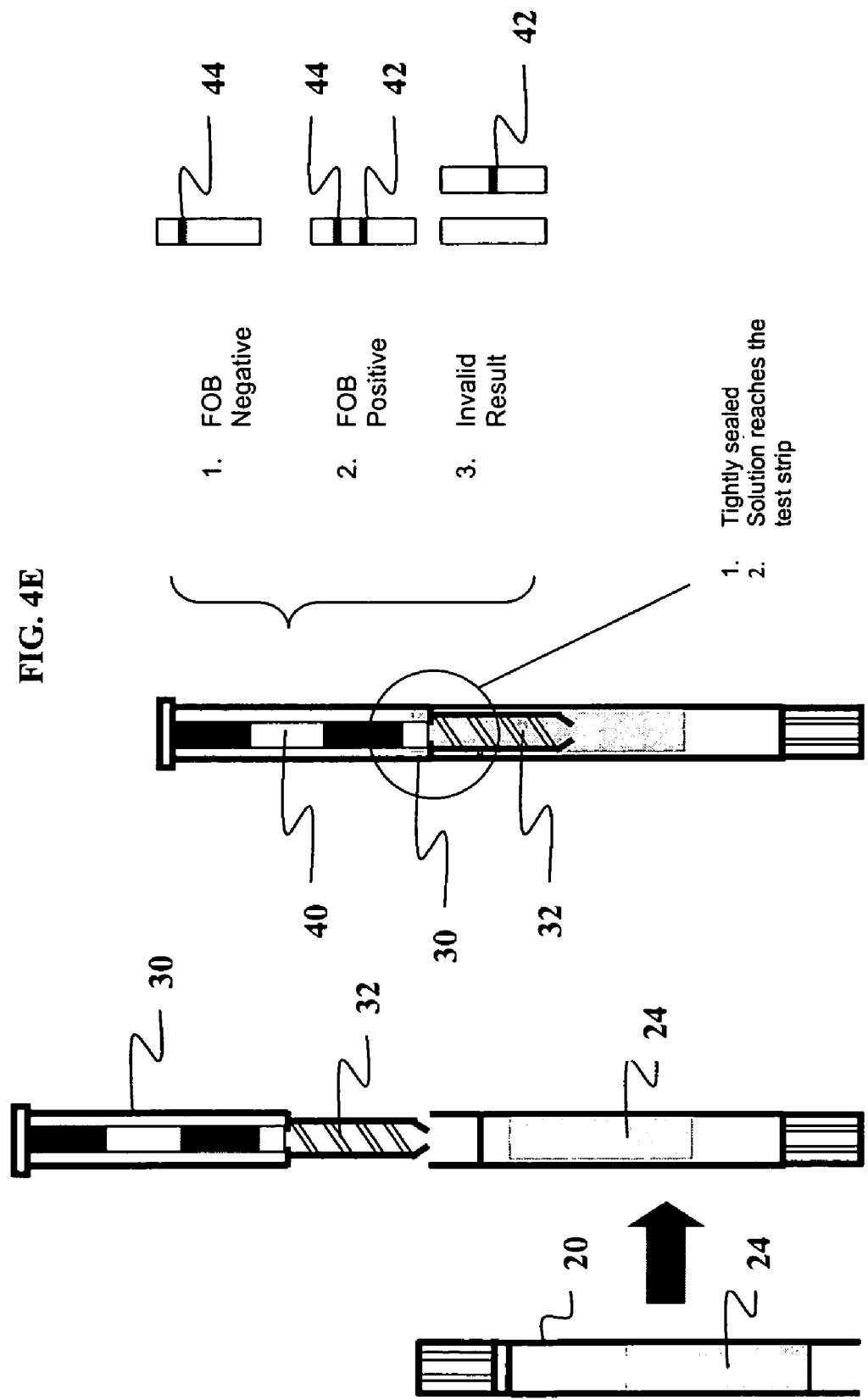

FECAL SAMPLE TEST DEVICE AND METHODS OF USE

CROSS REFERENCE TO RELATED APPLICATIONS

This patent application claims benefit of priority to U.S. patent application Ser. No. 60/653,345 filed on Feb. 16, 2005 and is herein incorporated by reference in its entirety.

TECHNICAL FIELD

The present invention relates generally to the field of immunoassay test devices. More specifically the present invention relates to a fecal sample immunoassay test device and methods of use.

BACKGROUND

Fecal sample testing is useful in detecting, diagnosing and monitoring a variety of diseases. For example, a fecal occult blood (FOB) test allows the detection of an unapparent bleeding beforehand, which may be an early sign of colon-rectal cancer, polyps or inflammatory bowel disease such as Crohn's disease, colitis ulcer, etc. A fecal *H. pylori* antigen test is able to aid the diagnosis of active infectious of *H. pylori* and monitor the effectiveness of the treatment. Other fecal pathogen tests such as the detection of specific antigen of rotavirus, adenovirus, *Giardia lamblia, Cryptosporidiun parvum* and *Entamoaba histolytica*, etc. are useful in the aid of disease diagnosis and monitor the effectiveness of the treatment. A fecal pancreas elastase-1 test or a fecal chymotrypsin test may aid in the diagnosis of pancreas excretory function. Immunoassays are used for analysis of these specific protein markers.

Recently, immunochromatographic test methods have simplified the immunoassay test procedures and have made such tests less complex. The test can be performed in low-grade clinical laboratories without the high complexity of automated immunoassay systems. This type of assay device is often referred to as a point-of-care test (POCT) device, which is frequently used in the physician's office. Some of the immunochromatographic test devices are also available over the counter (OTC) for consumers to perform the test on site or at home. These tests include urine pregnancy test, ovulation test, some types of drug of abuse tests, etc. Both POCT and OTC test devices are less complex than previous tests such as traditional radioimmunoassay, ELISA, chemiluminescence immunoassay, etc. and are simple and reliable to use.

Although there is POCT for fecal samples such as FOB test device, fecal rotavirus test device, fecal adenovirus test device, fecal *H. pylori* antigen test device, these test devices are still too complex to be performed with fecal samples by less skilled person without chemistry or laboratory training. The current available fecal sample POCT device is an open test system that includes a fecal sample collection tube with a sample collection strip. After a fecal sample is collected and diluted with a buffer in the collection tube, one is required to transfer a portion of the diluted fecal sample to the fecal POCT strip or cassette device. Therefore, the sample must be exposed to an open test environment. This open test system allows the fecal sample to openly enter the test environment and leak the bad smell. It increases the possibility of potential cross contamination of fecal sample and minimizes the safety and protection for test performer, as well as others working in the same environment. In addition, it is also unpleasant in handling the fecal sample test with this open test system.

Current devices require the transfer of a relatively precise amount of the test sample to an immunochromatographic test cassette/device during the testing procedure. The timing of sample application to the sample pad of the Immunochromatographic test cassette/device is also critical. Therefore, if the test is performed by persons lack of laboratory training in physician's office lab or nursing homes, some problem and mistake may arise during the using of this traditional Immunochromatographic test cassette/device. Moreover, if this type of test cassette/device is use by lay person as an OTC product, because the majority of consumers are not laboratory skilled and are not trained how to perform an immunochromatographic test, unexpected technical problems and mistakes may arise during the using of OTC test device. Therefore there is a need for a fecal test device having a simpler design for less laboratory skilled professionals or laypersons or the home consumer.

SUMMARY

The present invention recognizes the difficulty in performing previous fecal sample based assays and provides related benefits. In one aspect of the present invention a fecal test device is disclosed including a sample collection structure, a sample collection housing capable of reversibly housing the sample application structure, the sample collection housing including a puncturable barrier and a fecal suspension solution capable of substantially dissolving a fecal sample and stabilize the target analyte in the feces, a detection housing including a piercing or puncturing structure capable of puncturing the puncturable barrier, a labeled analyte binding compound capable of binding an analyte of interest, the detection housing capable of attachment to the sample collection housing such that the sample collection housing and the detection housing are in fluid communication, a labeled analyte binding compound capable of binding an analyte of interest, the labeled analyte binding compound positioned within said detection housing or the puncturing structure, the labeled analyte binding compound provided in a dried state and is capable of suspension upon exposure to the fecal suspension solution, and an analyte detection means capable of detecting a compound bound to the labeled analyte binding compound, the analyte detection means being positioned within said detection housing.

In one embodiment the sample collection structure is integrated with a removable cap portion of the sample collection housing. The puncturable barrier may include a plastic film adhered to the sample collection housing or to a cap of the sample collection housing. The puncturable barrier may cover an aperture that accesses the sample collection housing.

The fecal suspension solution may be a solution such as a sodium chloride solution or a sodium phosphate solution or tris hydrochloride, etc. The detection housing may attach to the sample collection housing by puncturing the puncturable barrier with the piercing or puncturing structure. Further more, the puncturing maneuver is a direct "push-in" process or a "screw-in" process.

In preferred embodiments, the analyte detection means is an immunochromatographic detection test strip. The analyte detection means may include a sample application portion and a detecting zone or a test zone or a control zone. The detection zone may include a membrane coated in part with an immobilzed compound such as an analyte specific antibody or an analyte specific antibody fragment, an analyte binding partner, a same analyte.

The labeled analyte binding compound may be a dried particle conjugate mass freely positioned in the bottom of the detection housing or positioned within a region of a puncturing structure, which is not necessary in physical contacting or attaching to the detection mean. In some embodiments, the dried particle conjugate is a lyophilized ball or sphere. The dried particle conjugate may also be a vacuum or oven-heat dried mass associated with a supporting material such as glass fiber, paper pad, chemicals, carbohydrates and proteins. The analyte of interest may include fecal occult blood, calprotectin, rotavirus antigen, adenovirus antigen, *Giardia lamblia, Cryptosporidium parvum, entamoeba histilica, H. pylori* antigen, pancreas elastase-1, lysozyme or alpha-1 antitripsin.

In another aspect of the present invention a fecal test immunoassay is disclosed including providing the fecal test device of the present invention, collecting a sample suspected of including an analyte of interest with the sample collection structure, inserting the sample collection structure into the sample collection housing thereby exposing the fecal sample to the fecal suspension solution, optionally inverting the sample collection housing, attaching the detection housing to the sample collection housing, and detecting the analyte of interest.

BRIEF DESCRIPTION OF THE FIGURES

FIG. 1 depicts a fecal test device 10 of the present invention.

FIGS. 4A-4E depict a pictorial representation of obtaining a sample 50 for the test device 10. The sample collection structure 18 is removed from the sample collection housing 20. The sample 50 is collected by the sample collection structure 18. The sample collection structure 18 is reinserted into the sample collection housing 20 and exposed to the fecal suspension solution 24 for suspension. The detection housing 30 is attached to the sample collection housing 20 causing the sample collection housing to pressurize forcing the fecal suspension solution 24 to flow through the piercing structure 32 into the detection housing 30. The fecal suspension solution 24 contacts the analyte detection means 40 where the test zone 42 and control zone 44 indicate negative, positive or invalid results.

DETAILED DESCRIPTION

Figure 1A:
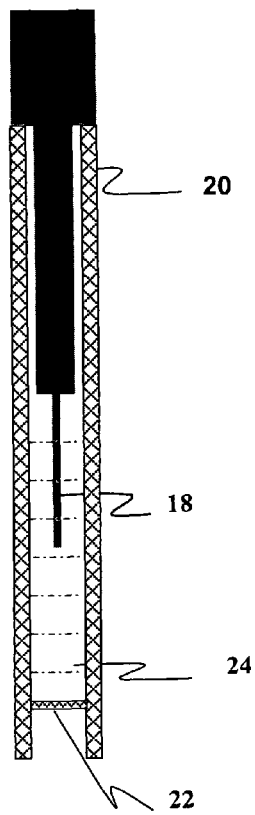
Referring to FIG. 1A, the device 10 includes a sample collection structure 18, a sample collection housing 20 including a puncturable barrier 22 and a fecal suspension solution 24.

The present invention includes a fecal test device 10 for detection of an analyte in a fecal sample 50. The fecal test device 10 includes a reversibly attachable sample collection portion for receiving a fecal sample and a sample detection portion for detection of an analyte in the fecal sample. In the preferred embodiment, the device operates by collecting a fecal sample 50 in a collection housing 20 where a fecal suspension solution 24 substantially solublizes the sample 50. Attachment of the detection housing 30 to the collection housing 20 pressurizes the collection housing 20 forcing the suspended fecal sample upwards into the detection housing 30. The suspended sample rehydrates a dried labeled analyte detection compound and the specificity of the labeled analyte binding compound for the analyte causes an analyte-analyte binding compound complex. The complex migrates upward along a analyte detection means 40 by capillary flow such as up an immunochromatographic test strip where the complex is captured by an immobilized compound having affinity for the analyte or analyte-analyte binding compound complex. The visual presence or absence of the label at the detection zone or test result zone 42 qualitatively determines whether the analyte is present and optionally quantitatively in what amount.

More specifically the test device 10 may include a sample collection structure 18, a sample collection housing 20 capable of reversibly housing the sample collection structure 18, a fecal suspension solution 24, a detection housing 30 capable of attaching to the sample collection housing 20, a labeled analyte binding compound 36 capable of finding an analyte of interest and an analyte detection means 40 capable of detecting or binding an analyte. The analyte detection means 40 is positioned within the detection housing 30. The sample collection housing 20 and the analyte detection housing 30 are in fluid communication when attached and the pressure difference within the device 10 causes the flow of the fecal suspension generally upward into the detection housing 30 allowing contact with the labeled analyte binding compound 36 and analyte detection means 40. Multiple or more than one analyte detection means 40 can be positioned together in one detection housing 30. The shape of detection housing 30 may be a round tube, a triangle tube, or a multi-side shaped tube. The detection housing 30 may display one or more detection means 40 on each side.

The fecal test device 10 of the present invention is a closed or a substantially closed system. The present invention permits the detection of an analyte in a fecal sample 50 while limiting exposure of the fecal sample 50 to the outside environment. The fecal test device 10 may be used by professionals in a clinical laboratory or a physician's office, or by consumers (lay persons) at home.

The device 10 of the present invention may be used to detect a variety of analytes within a fecal sample 50 or other biological sample and can therefore be used to detect a variety of medical conditions. The fecal test device may detect a single analyte in a fecal sample 50 or other biological sample or may detect two or more analytes simultaneously or substantially simultaneously. For example, analytes of particular interest may include but are not limited to Fecal Occult Blood, calprotectin, rotavirus antigen, adenovirus antigen, *Giardia lamblia, Cryptosporidium parvum, entamoeba histilica, H. pylori* antigen, pancreas elastase-1, lysozyme and alpha-1 antitripsin. The present test device may be used to detect a variety of medical conditions or to detect disorders within the gastrointestinal system, as well as pancreatic and hepatic disorders.

Sample Collection

The fecal sample collection portion includes a sample collection housing 20 and a sample collection structure 18. The sample collection structure 18 is optionally integrated to a housing cap or lid. Thus, at one end of the sample collection housing 20 is a housing cap or means to fluidly seal the collection portion. The cap may be any suitable cap such as a plastic screw cap or snap cap allowing the sample housing to be reversibly or irreversibly sealed. Preferably the housing cap seals the collection housing 20 such that it is fluid tight or does not leak fluid. The sample collection housing 20 may be constructed from any suitable material such as polystyrene or polypropylene and may be formed using injection molding techniques known in the plastic arts. Similarly, housings of the present invention including the sample collection housing 20 and detection housing 30 may be constructed using techniques known in the injection molding and plastic arts.

The fecal sample 50 is collected using a sample collection structure 18. The sample collection structure 18 may be any suitable structure for obtaining or collecting a fecal sample 50 and placing it 50 in the sample collection housing 20. Examples include but are not limited to a wand, a tube, a spatula and the like. The sample collection structure 18 may be a hollow or solid elongated tube or a cross-shaped column. In a preferred embodiment the fecal collection structure 18 is connected or integrated with the housing cap. The fecal collection structure 18 may assist in suspending the fecal sample 50 in a solution 24 by agitating the solution 24 within the collection housing 20. The sample collection structure 18 may be constructed from any suitable material such as plastics, metal alloy and the like. In preferred embodiments, the sample collection structure 18 is constructed from a plastic such as polypropylene or polystyrene.

The fecal sample 50 is suspended or diluted in a fecal suspension solution 24 or dilution solution within the collection housing 20. The suspension or dilution solution 24 may be a buffer solution at a particular pH or may include one or more sugars or components to assist in the migration of one or more analytes within the fecal sample 50 along, on top of or within an analyte detection means 40. The solution 24 may include sodium chloride and/or sodium phosphate such as PBS (phosphate buffered saline) or Tris-hydrochloride and may include one or more preservative agents, as well as protein matrix such as bovine serum albumin, and detergents such as tween-20 and triton X-100. The fecal suspension solution 24 may be prepared using standard chemical techniques and may vary depending on the analyte binding compound 36 or analyte of interest. The volume of suspension or buffer solution may vary depending on the amount of biological sample such as blood, a bodily fluid, a bodily tissue and the like and the volume of the sample collection housing 20. The suspension or buffer solution 24 should be capable of substantially suspending or buffering the desired fecal sample 50. The fecal suspension solution 24 should be sufficient to dissolve or suspend enough fecal sample 50 to allow detection of the desired analyte. Thus, an analyte in high abundance may not require as much fecal suspension solution 24 as an analyte in low abundance.

Figure 1B:
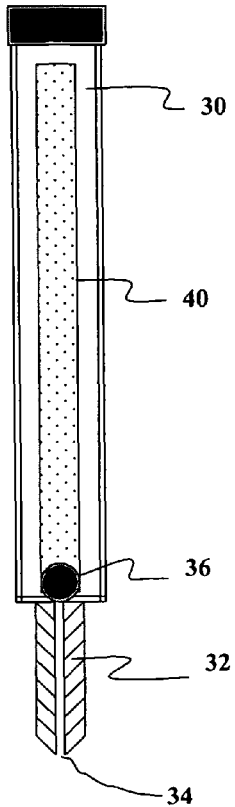
Referring to FIG. 1B, the device 10 also includes a detection housing 30 with an integrated piercing structure 32 and a sample flow aperture 34, a labeled analyte binding compound 36 and an analyte detection means 40.
Figure 1C:
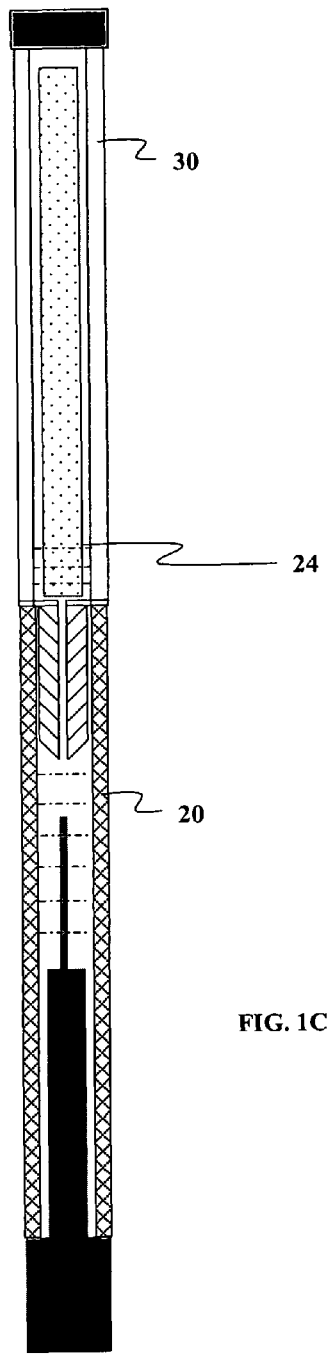
FIG. 1C depicts the attachment of the sample collection housing 20 to the sample detection housing 30 such that the sample collection housing 20 and the sample detection housing 30 are in fluid communication.
Figure 2:
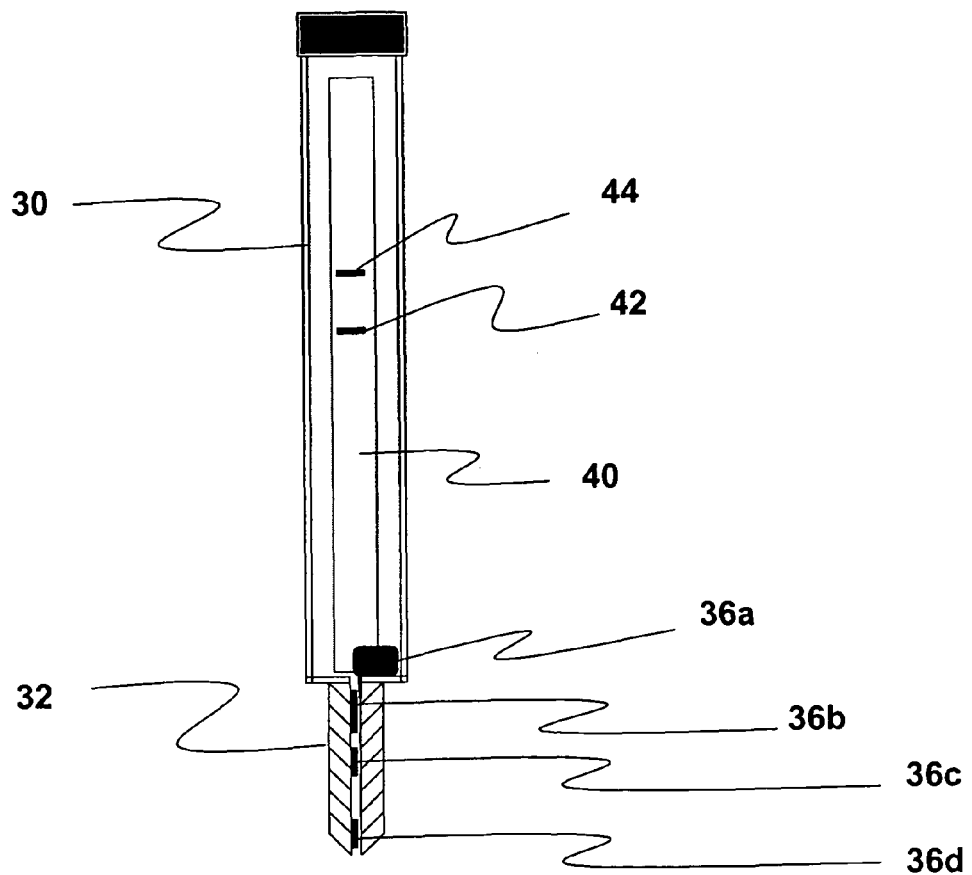
FIG. 2 also depicts a view of the detection housing 30 to demonstrate the labeled analyte binding compound 36 may be positioned at the bottom of the detection housing 36*a*, or within the piercing structure 32 such as a top portion 36*b*, a middle portion 36*c*, or a bottom portion 36*d*. Also shown is an analyte detection means 40 with a test result zone 42 and a control zone 44.
Figure 3A:
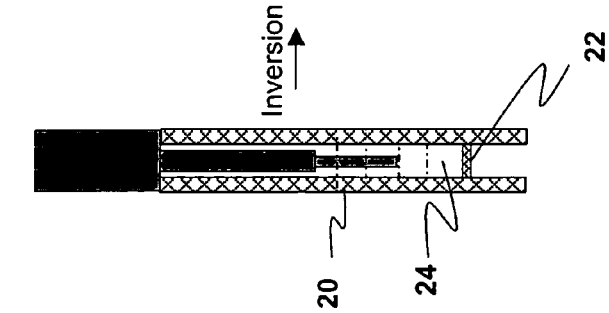
FIGS. 3A-3C depict a pictorial representation of using a fecal test device 10. The sample collection structure 18 is inserted into the sample collection housing 20, which contains the fecal suspension solution 24. The sample collection housing 20 is inverted. The piercing structure 32 punctures the puncturable barrier 22 and is slidably inserted into the sample collection housing 20. The fecal suspension solution 24 flows upward through the piercing structure 32 and through the sample flow aperture 34. The fecal suspension solution 24 is exposed to the analyte detection 40 means for detection.
Figure 3B:
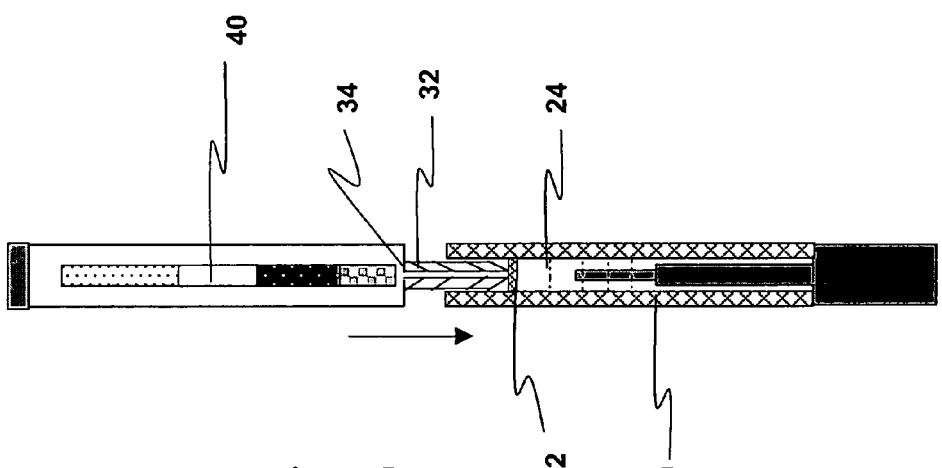
Figure 3C:
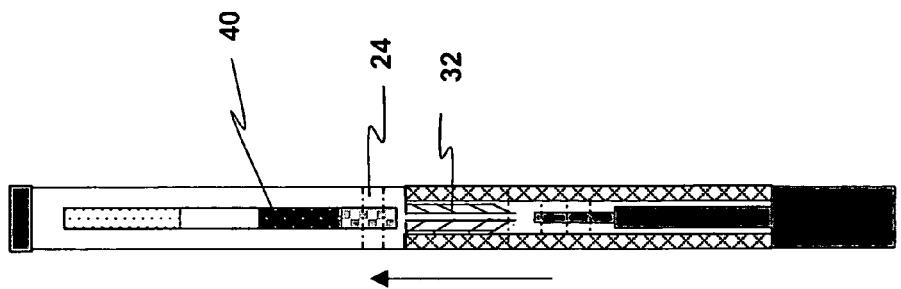
Figure 5:
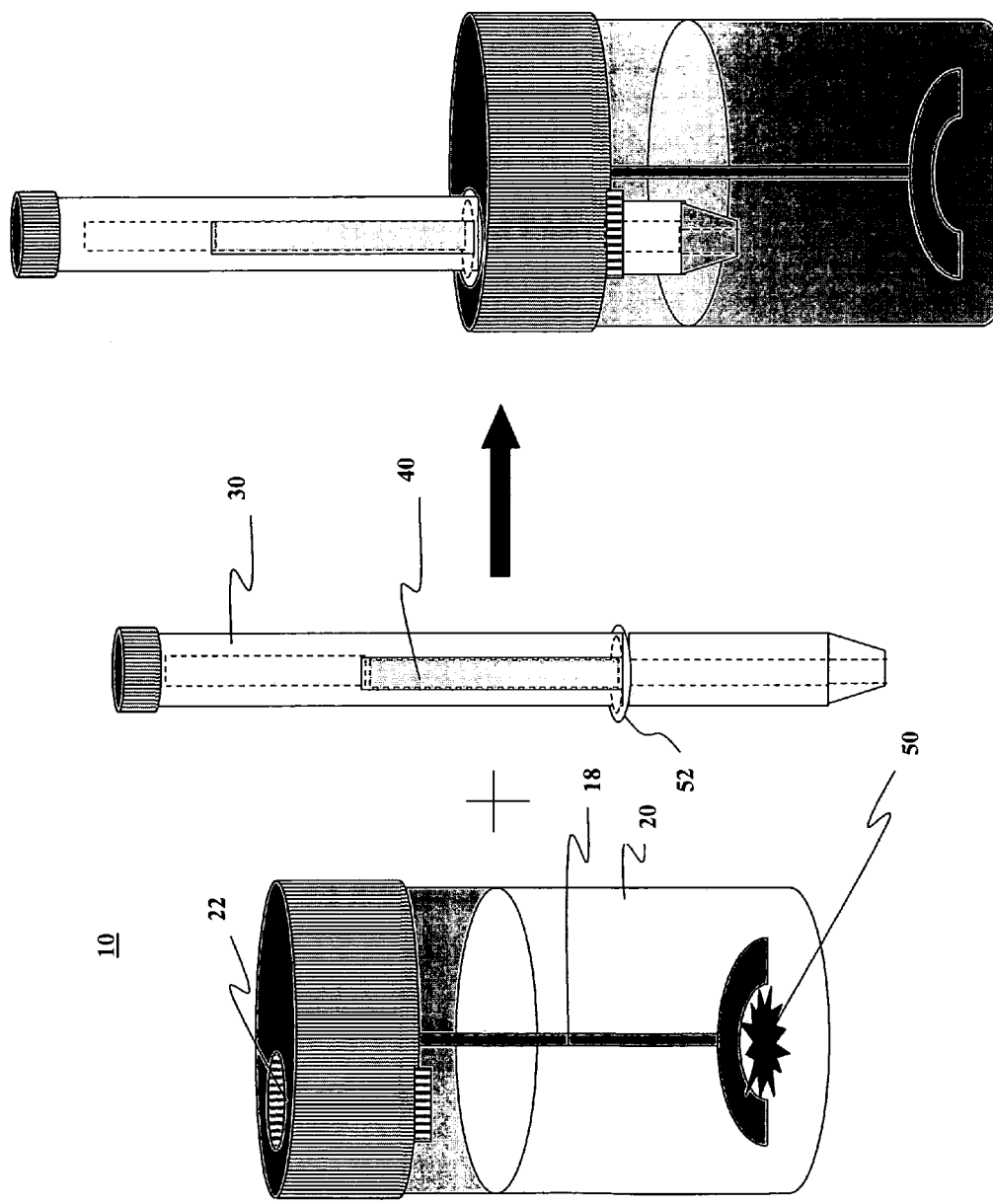
FIG. 5 depicts another embodiment of the fecal test device 10 including a fecal sample collection housing 20 having a puncturable barrier 22 positioned along the screw cap. The detection housing 30 is capable of engaging the sample collection housing 20 through the puncturable barrier 22. An O-ring 60 is positioned generally about the detection housing 30.

The collection housing 20 also includes a puncturable barrier 22. The puncturable barrier 22 prevents a collected sample 50 from exiting the collection housing 20 until the detection housing 30 or piercing structure 32 is properly attached. The puncturable barrier 22 may be at an end opposite the screw cap (see for example FIGS. 1-4). The puncturable barrier 22 may be flush with an end of the sample collection housing 20 or may be recessed within the housing 20. Examples of suitable materials include any puncturable film or wrap capable of retaining an aqueous solution such as but not limited to a plastic wrap, PARAFILM, aluminum wrap or multi-layer film structure and the like. The puncturable barrier 22 may be formed by annealing the puncturable barrier 22 about the perimeter of an aperture positioned on the sample collection housing 20 or housing cap such as by melting a perimeter of the puncturable barrier 22 and annealing it 22 to the collection housing 20. Piercing or puncturing of the barrier 22 exposes the aperture for insertion of the piercing structure 32.

Analyte Detection

The detection housing 30 permits entry of the suspended or diluted fecal sample 50 or biological sample and performs the desired assay. The detection portion includes a detection housing 30 including a piercing structure 32 (also referred to as a puncturing structure) or a piercing region and an analyte detection means 40 or an adaptation structure for insertion of an analyte detection means 40. The detection housing 30 may be constructed from a variety of materials such as but not limited to injection molded plastic such as polystyrene and polypropylene. Preferably the detection housing 30 is manufactured from a transparent or semi-transparent material such as polystyrene or polypropylene such that the analyte detection means 40 may be viewed without opening the detection housing 30. The size, shape and volume of the detection housing 30 may vary depending on the desired assay.

A piercing structure 32 may extend substantially outward as depicted in FIGS. 1-4. The piercing structure 32 is capable of piercing the puncturable barrier 22 of the collection housing 20. The piercing structure 32 may be threaded complementary to an aperture of the sample collection housing 20 such that attachment of the two portions involves screwing the piercing structure 32 into the sample collection housing 20 and through the puncturable barrier 22. Alternatively, the piercing structure 32 may be slidably inserted into the collection housing 20. In the preferred embodiment the detection housing 30 is attached above the sample collection housing 20. Attachment of the detection housing 30 to the sample collection housing 20 causes atmospheric pressure within the sample collection housing 20 to increase resulting in fluid flow from the sample collection housing 20 to the detection housing 30. The physical presence of the piercing structure 32 within the sample collection housing 20 displaces fluid from the sample collection housing 20 to the detection housing 30. The detection housing 30 includes a sample flow aperture 34 permitting a liquid extracted sample to flow from the sample collection housing 20 into the detection housing 30 optionally through the piercing structure 32. Flow of a suspended or diluted sample occurs by pressurizing the collection housing 20 via insertion of the piercing structure 32.

An analyte detection means 40 is positioned within the detection housing 30. The structure of the analyte detection means 40 may be provided as a strip of nitrocellulose membrane coated with antigen specific monoclonal or polyclonal antibodies as a test zone 42 or test line and optionally an anti-species antibody (IgG, IgM, IgA) specific antibody as a control zone 44 or control line (See FIG. 2). There is no sample application portion or pad necessary, however the present invention may be adapted to include a sample application portion, sample pad or absorption pad if desired. There is not a requirement for a conjugate pad or a labeling portion directly or physically attached to the structure of the detection means 40, however the present invention may be adapted to include a conjugate pad or labeling portion if desired.

A labeled analyte binding compound 36 such as an analyte specific antibody or fragment thereof including Fab or Fab'2, kappa or lambda light chain, heavy chain, polyclonal or monoclonal antibody, analyte binding partner or a same analyte is conjugated to visually identifiable particle, such as colloid gold particle, latex particle in the size of 10 nm to 120 nm per particle. Preferably the labeled analyte binding compound 36 is a particle-conjugated antibody, which may be further processed via lyophilization (such as but not limited to a lyophilized ball or sphere), oven drying and vacuum drying to become a non-liquid pallet or structure. The particle-antibody conjugate may be dried without any physical support by forming a pallet in a different shape. The particle-antibody conjugate may be dried with a piece of support material such as but not limited to a piece of glass fiber, paper pad, a chemical, a carbohydrate, a protein, etc. The dried particle-antibody conjugate may be freely positioned in the bottom 36*a* of the detection housing 30 such that the conjugated antibody is not solidly attached to the detection means 40. Alternatively, the dried particle-antibody conjugate is freely positioned within or adhered to a region of the piercing structure of the detection portion. In other embodiments, the labeled analyte binding compound 36 is positioned within the upper 36*b*, middle 36*c* or lower portion 36*d* of the piercing structure 32.

When the detection housing 30 is attached to the sample collection housing 20, a portion of liquid extracted sample is capable of flow from the sample collection housing 20 to the bottom region of the detection housing 30. During this liquid flowing process, the liquid extracted sample re-hydrates the particle-antibody conjugate (or labeled analyte binding compound 36) before or at about the same time as the liquid extracted sample reaches the analyte detection means 40. A portion of analyte in a test sample 50 binds to the particle-conjugated antibody before the analyte migrates along the detection means 40. Another portion of analyte in a test sample 50 may bind to the particle-conjugated antibody during analyte migrating on the detection means 40.

An analyte detection means 40 is positioned within the detection housing 30 and permits the detection of at least one analyte from the fecal sample 50. The analyte detection means 40 may be a test strip such as an immunochromatographic test strip or have a cassette-like configuration. Non-limiting examples of such test strips and cassettes are known in the analyte detection art and typically include a sample application portion, a labeling portion and a capture portion. As non-limiting examples: U.S. Pat. No. 5,073,484 by Swanson et al.; U.S. Pat. No. 5,654,162 by Guire et al.; U.S. Pat. No. 6,020,147 by Guire et al.; and U.S. Pat. No. 5,622,871 by May et al disclose a variety of analyte detection configurations that may be used with the present invention and are herein incorporated by reference in their entirety. The referred to test strips may be used as-is or may be modified by omitting a step of coating the test strip or portion of a test strip with a mobile labeled binding compound and/or removing a sample pad or absorption pad. A test strip that omitting of a step of coating the test strip or portion of a test strip with a mobile labeled binding compound is not a workable immunochromatographic test device in the detection of a target analyte according to the disclosure described in the literatures and prior patents. However, combining the sample collection housing 20 and detection housing 30 with a mass of labeled binding compound 36 pre-assembled within the detection housing 36*a,b,c,d*, but not physically attached to a detection mean 40 that lack of a mobile conjugate or labeled compound, the test strip that omitting of a step of coating the test strip or portion of a test strip with a mobile labeled binding compound is fully workable and functional in the detection of a target analyte. As non-limiting examples, the analyte detection means may be a fecal occult blood test strip, *H. pylori* antigen test strip, pancreas elastase-1 test strip, lysozyme test strip, alpha-1 antitripsin test strip, rotavirus antigen test strip, adenovirus antigen test strip, *giardia lamblia* antigen test strip, *cryptosporidium parvum* antigen test strip, amoeba antigen test strip and the like. The capture or labeling regions of an analyte detection means of the present invention may utilize a monoclonal antibody, a polyclonal antibody, a f(ab) or f(ab)'2 fragment, or a compound capable of binding the analyte of interest. Similarly, the present invention may utilize latex beads, colloid gold particles and the like for visualization of results. IND Diagonstics provides a FOB test, which may be adapted for use with the present invention. One or more detection means 40 may be used within the same detection housing 30. When two or more detection means 40 are provided, one, two or more analytes may be detected. When two or more detection means are provided within the same detection housing 30, one, two or more detection means with different test sensitivity or cut-off for the same analyte may be used as a semi-quantitative test method. Two or more detecting means 40 may be configured back-to-back, side to side and the like.

In other embodiments the present invention is provided without a detection means. In this embodiment, the present invention includes an adaptation capable of receiving an immunochromographic test strip. The test strips that may be used in this embodiment are any generally elongated test strips such as those referred to as prior documents under detection means.

The device 10 of the present invention may also utilize competition immunoassay technology such as binding the immobilized binding compound to a second analyte having the same or different affinity or avidity to the immobilized binding compound. Alternatively, a labeled second analyte (or competition analyte) may be bound to the immobilized analyte binding compound or analyte binding compound. In this example, the analyte of interest may have a high affinity or avidity to the immobilized compound or analyte binding compound causing the analyte of interest to displace the second analyte. Capture or noncapture of the labeled second analyte may be indicative of qualitative analysis or quantitative analysis of the analyte of interest.

The present invention also includes a method of conducting a fecal test immunoassay for an analyte of interest. The method may include providing any of the disclosed fecal test devices 10, collecting a fecal sample 50 suspected of including an analyte of interest with the sample collection structure 18, inserting the sample collection structure 18 into the sample collection housing 20 thereby exposing the fecal sample 50 to the fecal suspension solution 24, optionally inverting the sample collection housing 20, and detecting the analyte of interest. As provided earlier, the analyte may bind the analyte binding compound 36 within the piercing structure 32 or within the detection housing 30. The method may also include mixing the labeled analyte binding compound 36 with a competition analyte (also called a second analyte) prior to exposing the analyte binding compound 36 to the analyte of interest.

The method qualitatively determines there is an analyte of interest present when an analyte-labeled analyte binding compound is captured by an immobilized detecting compound, preferably in a detection zone 42 on a test strip, or if a labeled competition analyte is released from the mobile analyte binding compound and the labeled competition analyte is captured by an immobilized capture compound, or if a labeled competition analyte pre-bound to the immobilized capture compound is released.

As can now be envisioned, the test device 10 and methods of the present invention may also include a variety of control zones 44 on the analyte detection means 40. The control zone 44 functions as a control to inform the user whether or not the test device 10 is operating properly. The control zone 44 may include an immobilized compound capable of capturing a labeled analyte binding compound 36 and the like. The control zone 44 may include a labeled analyte of interest to verify the ability of the mobilized analyte binding compound 36 to bind the analyte.

A quantitative or semi-quantitative test result can be obtained by identify the color intensity of a test line. Methods of identify the color intensity include visual comparison of a test line color intensity to a control line color intensity on the same detection mean, identify the color intensity of a test line to an existing color strip standard, and identify the color intensity of a test line via an electronic sensor or color reader, etc.

EXAMPLES

Example 1

Colloid Gold Labeled Anti-human Hemoglobin Antibody

Colloid gold labeled monoclonal anti-human hemoglobin antibody in a protein buffer matrix with an OD 10 at 520 nm on spectrophotometer is soaked with a piece of glass fiber. The antibody soaked glass fiber is dried in an oven or a vacuum dryer. Assemble the dried colloid gold labeled antibody glass fiber to the position of the bottom 36a or within the aperture 36b,c,d of the puncturable structure of the detection housing 30. This detection housing must be stored at a low humidity (less than 40%) condition for further assembling the fecal occult blood test strip.

Example 2

Fecal Occult Blood Test Strip

A fecal occult blood test strip is a detection means 40. One can use HF-135 nitrocellulose (Millipore Corporation) and coat the membrane with a significant amount of monoclonal anti-human hemoglobin antibody (this antibody must be paired with the labeled antibody to form a "sandwich" assay known in the art of immunoassay) as test line and a goat anti-mouse IgG antibody as a control line. The said membrane is laminated with a supporting or backing card and cut into 70 mm long and 4 mm width. The test line located at the 35 mm from the bottom end of the membrane strip and the control line located at the 40 mm from the bottom end of the membrane strip. There is not sampling pad, absorption pad, conjugate pad and labeled anti-human hemoglobin antibody attached to the said membrane. Dipping this antibody coated strip into a fecal sample extraction contains significant amount (greater than 1000 ng/ml) of human hemoglobin, there is no any signal can be observed both in the test line and the control line. One assembles the said membrane strip into the detection housing of example 1 and sealed the detection housing with a desiccant in a pouch.

Example 3

Utilizing the Fecal Test Device

Referring to FIGS. 1-4, the integrated cap and sample collection structure are unscrewed from the fecal sample collection housing and a portion of the fecal sample is collected using the sample collection structure. The fecal sample is placed in the collection housing and the screw cap is screwed back on. The fecal sample is suspended in a pre-added fecal suspension solution or dilution buffer. One may gently shake the collection device to substantially dissolve the collected sample with the suspension solution or dilution buffer. At this point, the fecal sample may either be transported to a test facility, such as a clinical laboratory, a physician's office, etc., for testing or be tested right at a site.

The sample collection housing is optionally inverted (depending on the particular embodiment). The puncturable barrier of the sample collection housing is pierced by insertion of the piercing structure of the detection housing of example 2. The resuspended or diluted sample is permitted to flow through the sample flow aperture into the detection housing. The fecal suspension fluid rehydrates the dried labeled binding compound (colloid gold labeled anti-human hemoglobin monoclonal antibody) of example 1. The labeled binding compound binds the analyte (human hemoglobin) of interest and migrates upward along the detection means via capillary flow. An immobilized capture compound (coated anti-human hemoglobin monoclonal antibody) captures the analyte bound to the labeled binding compound. After a predetermined test period, which is usually from about two (2) to about thirty (30) minutes in time, the results are viewed from the capture region and through detection housing.

I claim:

1. A fecal test device comprising:
   a. a sample collection structure;
   b. a sample collection housing comprising a puncturable barrier, wherein said sample collection housing is capable of reversibly housing said sample collection structure;
   c. a fecal suspension solution capable of substantially dissolving or solublizing a fecal sample, wherein the dissolved or solublized fecal sample may be stored in said sample collection housing for later testing;
   d. a detection housing comprising a piercing structure positioned at the bottom of said detection housing, said piercing structure capable of piercing through said puncturable barrier, wherein said detection housing is capable of attachment to said sample collection housing by insertion of said piercing structure through said puncturable barrier and into said collection housing, wherein upon attachment said sample collection housing and said detection housing are in fluid communication, further wherein upon attachment said fecal suspension solution is volumetrically displaced upwards and against gravity from said sample collection housing into said detection housing by the presence of said piercing structure;
   e. a labeled analyte binding compound capable of binding an analyte of interest, further wherein said labeled analyte binding compound is provided in a dried state and is capable of suspension upon exposure to said fecal suspension solution; and f. an analyte detection means capable of detecting said analyte of interest bound to said labeled analyte binding compound, wherein said analyte detection means is positioned entirely within said detection housing for upward migration of said fecal suspension solution;

wherein the fecal test device comprises a storage configuration and a detection configuration, further wherein said storage configuration comprises:
  i) said sample collection housing detached and free from contact from said detection housing thereby preventing fluid communication, and
  ii) said sample collection structure, fecal sample and fecal suspension solution housed within said sample collection housing;

further wherein said detection configuration comprises:
  i) said sample collection housing attached to said detection housing, and
  ii) said sample collection housing, detection housing and analyte detection means in vertical alignment, further wherein said sample collection structure is free from contact with said detection housing;

further wherein the test device is a closed system in both said storage configuration and said detection configuration, which prevents exposure of said fecal sample to the outside environment in each configuration.

2. The fecal test device according to claim 1, wherein said sample collection structure is integrated with a removable cap portion of said sample collection housing.

3. The fecal test device according to claim 2, wherein said puncturable barrier comprises a plastic film adhered to said sample collection housing, wherein said puncturable barrier covers an aperture positioned at an end of said sample collection housing opposite said removable cap portion, further wherein said aperture accesses said sample collection housing wherein pierced.

4. The fecal test device according to claim 1, wherein said fecal suspension solution is selected from the group consisting of a sodium chloride solution, a sodium phosphate solution and a tris hydrochroride solution.

5. The fecal test device according to claim 1, wherein said insertion of said piercing structure comprises a piercing maneuver comprising a screw in process.

6. The fecal test device according to claim 1, wherein said detection housing is transparent and provided in a shape selected from the group consisting of cylindrical, triangular, pyramidal, pentagonal, hexagonal, heptagonal, and octagonal; further wherein said detection housing fluidly communicates with said sample collection housing via a fluid communication channel within said piercing structure.

7. The fecal test device according to claim 1, wherein said detection housing is positioned above said sample collection housing.

8. The fecal test device according to claim 1, wherein said analyte detection means is an immunochromatographic detection test strip.

9. The fecal test device according to claim 1, wherein said test device comprises two or more analyte detection means.

10. The fecal test device according to claim 9, wherein two or more analyte detection means detect the same analyte, further wherein each of said at two or more analyte detection means comprises a different detection sensitivity or cut-off for the same analyte comprising an immobilized analyte binding compound, further wherein each of the immobilized binding compounds are provided in a different amount.

11. The fecal test device according to claim 9, wherein said two or more analyte detection means detect two or more analytes comprising different immobilized and analyte specific binding compounds.

12. The fecal test device according to claim 1, wherein said analyte detection means comprises a membrane strip with a detection zone that is not directly sunk into the fecal sample suspension solution, but is in contact with the fecal sample suspension solution via liquid chromatographic movement.

13. The fecal test device according to claim 11, wherein said detection means comprises a membrane coated in part with an immobilized binding compound selected from the group consisting of an analyte specific antibody or an analyte specific antibody fragment, an analyte binding partner, and a same analyte.

14. The fecal test device according to claim 1, wherein said analyte of interest is detected by the presence of said labeled analyte binding means along a portion of said detection means via an optical detection method or via an electronic means.

15. The fecal test device according to claim 1, wherein said labeled analyte binding compound is a lyophilized ball or sphere.

16. The fecal test device according to claim 1, wherein said labeled analyte binding compound is a vacuum or oven-heat dried mass associated with a supporting material.

17. The fecal test device according to claim 16, wherein said supporting material is selected from the group consisting of glass fiber, paper pad, chemicals, carbohydrates and proteins.

18. The fecal test device according to claim 1, wherein said labeled analyte binding compound is freely positioned within said detection housing, further wherein said labeled analyte binding compound is not physically attached to said detection means.

19. The fecal test device according to claim 1, wherein said labeled analyte binding compound is positioned on and physically attached to said detection means.

20. The fecal test device according to claim 1, wherein said analyte of interest is selected from the group consisting of fecal occult blood, calprotectin, rotavirus antigen, adenovirus antigen, *Giardia lamblia, Cryptosporidium parvum, entamoeba histolytica, H. pylori* antigen, pancreas elastase-1, lysozyme and alpha-1 antitripsin.

21. The fecal test device according to claim 1, wherein said displacement upwards and against gravity from said sample collection housing into said detection housing occurs by fluid flow through said piercing structure and through a sample flow aperture of said detection housing.

22. The fecal test device according to claim 21, wherein said labeled analyte binding compound is positioned within said piercing structure.

23. The fecal test device according to claim 8, further comprising an adaptation, wherein said adaptation accepts said immunochromatographic detection test strip.

24. The fecal test device according to claim 1, wherein an inner diameter of said detection housing is substantially the same as an inner diameter of said collection housing.

* * * * *